United States Patent
Ma et al.

(10) Patent No.: US 10,441,773 B2
(45) Date of Patent: Oct. 15, 2019

(54) PORTED CATHETER ADAPTER WITH INTEGRATED SEPTUM ACTUATOR RETENTION

(71) Applicant: Becton, Dickinson and Company, Franklin Lakes, NJ (US)

(72) Inventors: Yiping Ma, Layton, UT (US); Weston F. Harding, Lehi, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 17 days.

(21) Appl. No.: 15/872,602

(22) Filed: Jan. 16, 2018

(65) Prior Publication Data
US 2018/0140820 A1 May 24, 2018

Related U.S. Application Data

(63) Continuation of application No. 14/597,032, filed on Jan. 14, 2015, now Pat. No. 9,895,525.
(Continued)

(51) Int. Cl.
*A61M 39/10* (2006.01)
*A61M 25/06* (2006.01)
(Continued)

(52) U.S. Cl.
CPC ............ *A61M 39/10* (2013.01); *A61M 25/00* (2013.01); *A61M 25/0009* (2013.01);
(Continued)

(58) Field of Classification Search
CPC .. A61M 39/06; A61M 39/0693; A61M 39/22; A61M 39/26; A61M 2039/0633; A61M 2039/064; A61M 2039/066; A61M 2039/1072; A61M 2039/242; A61M 2039/2473; A61M 2039/2486; A61M 2039/261; A61M 2039/267
See application file for complete search history.

(56) References Cited

U.S. PATENT DOCUMENTS

| 7,008,404 B2 | 3/2006 | Nakajima |
| 2010/0051035 A1 | 3/2010 | Jenkins et al. |
(Continued)

FOREIGN PATENT DOCUMENTS

| CA | 2732838 | 2/2010 |
| CA | 2851235 | 4/2013 |
(Continued)

*Primary Examiner* — Bhisma Mehta
*Assistant Examiner* — James D Ponton
(74) *Attorney, Agent, or Firm* — Kirton & McConkie; Craig Metcalf; Kevin Stinger

(57) ABSTRACT

A ported catheter adapter and septum actuator having various features to prevent displacement and dislodging of the septum actuator when accessing the patient's vasculature via the inserted infusion device. In particular, the systems and methods of the present invention provide an intravenous infusion device incorporating a septum actuator with a retention tab that interacts with a retention ring that is incorporated into the valve of a side port. This interaction retains the septum actuator within the lumen of the catheter adapter, thereby allowing for subsequent access to the patient's vasculature.

24 Claims, 7 Drawing Sheets

Related U.S. Application Data

(60) Provisional application No. 61/929,686, filed on Jan. 21, 2014.

(51) Int. Cl.
| | |
|---|---|
| *A61M 25/00* | (2006.01) |
| *A61M 39/06* | (2006.01) |
| *A61M 39/00* | (2006.01) |
| *A61M 39/26* | (2006.01) |
| *A61M 39/24* | (2006.01) |

(52) U.S. Cl.
CPC .... *A61M 25/0097* (2013.01); *A61M 25/0606* (2013.01); *A61M 39/00* (2013.01); *A61M 39/0606* (2013.01); *A61M 39/0693* (2013.01); *A61M 39/26* (2013.01); *A61M 39/24* (2013.01); *A61M 2039/062* (2013.01); *A61M 2039/064* (2013.01); *A61M 2039/066* (2013.01); *A61M 2039/068* (2013.01); *A61M 2039/1072* (2013.01); *A61M 2039/266* (2013.01); *A61M 2039/268* (2013.01); *A61M 2205/0205* (2013.01); *Y10T 29/494* (2015.01)

(56) References Cited

U.S. PATENT DOCUMENTS

| | | |
|---|---|---|
| 2012/0065612 A1 | 3/2012 | Stout et al. |
| 2013/0090607 A1 | 4/2013 | McKinnon et al. |
| 2013/0090609 A1* | 4/2013 | Sonderegger ......... A61M 39/22 604/256 |
| 2013/0237925 A1 | 9/2013 | Trainer et al. |
| 2013/0310764 A1 | 11/2013 | Burkholz et al. |

FOREIGN PATENT DOCUMENTS

| | | |
|---|---|---|
| CN | 202844312 | 4/2013 |
| CN | 203263883 | 11/2013 |
| DE | 202007006190 | 8/2007 |
| JP | 2002-291906 | 10/2002 |
| JP | 2012-075939 | 4/2012 |
| WO | 2013/051242 | 4/2013 |

* cited by examiner

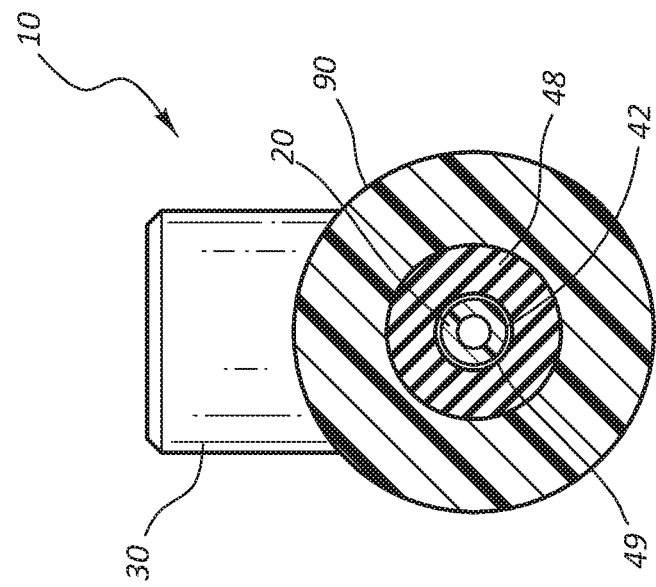
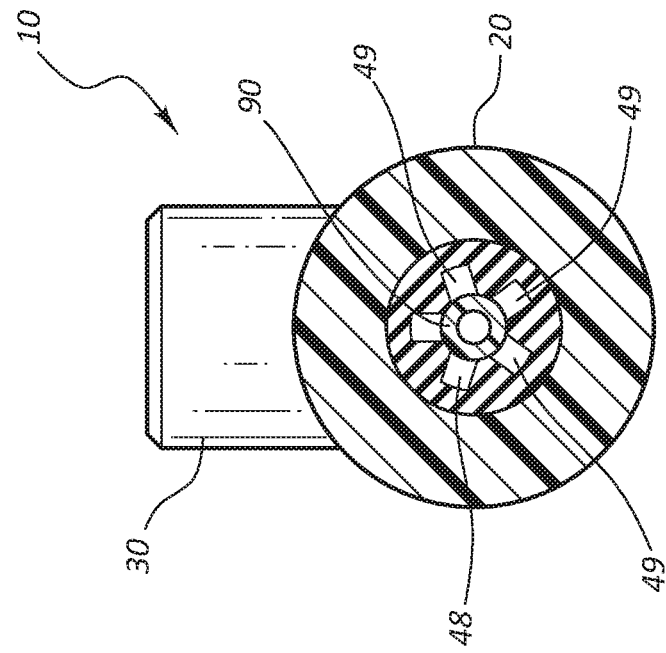

PORTED CATHETER ADAPTER WITH INTEGRATED SEPTUM ACTUATOR RETENTION

RELATED APPLICATIONS

This application is a continuation of U.S. patent application Ser. No. 14/597,032, filed Jan. 14, 2015, and entitled PORTED CATHETER ADAPTER WITH INTEGRATED SEPTUM ACTUATOR RETENTION, which claims priority to U.S. Provisional Patent Application Ser. No. 61/929,686, filed Jan. 21, 2014, and entitled PORTED CATHETER ADAPTER WITH INTEGRATED SEPTUM ACTUATOR RETENTION, which are incorporated herein in their entirety.

BACKGROUND

Intravenous infusion systems are commonly used to access the vasculature of a patient as part of an infusion therapy procedure. An intravenous infusion system generally includes a fluid reservoir of IV bag that is connected to the patient via an intravenous catheter. The catheter is commonly coupled to a catheter adapter having a Luer-lock connector, or other connector-type for coupling the catheter adapter to a syringe, a section of intravenous tubing, or some other external Luer device. Fluid from the IV bag flows into the patient via the catheter adapter and the intravenous catheter.

In some instances, the catheter adapter further includes a blood control septum that is positioned within a fluid pathway running though the catheter adapter. The blood control septum is provided to allow selective flow of fluid through the fluid pathway. For example, the blood control septum may include a slit that may be bypassed when an external Luer device is coupled to the catheter adapter and directly engaging the septum. Upon removing the external Luer device, the slit is closed to prevent blood from leaking out of the catheter adapter.

In some instances, the catheter adapter further includes a septum actuator that is contacted by the external or secondary infusion device, such as a Luer device, and advanced through the slit of the septum. The septum actuator is generally advanced through the septum to provide a temporary pathway through the septum. Upon removal of the secondary infusion device, the resilient nature of the septum backs the septum actuator out of the septum slit.

In some instances, the septum actuator is accidentally dislodged and displaced from the proximal opening of the catheter adapter, thereby preventing subsequent advancement through the septum. In this instance, the infusion device must be removed from the patient and replaced with a new device. Not only does this create an inconvenience for the care provider, this also results in increased risk of infection and trauma to the patient as a second catheterization is now required.

Thus, while systems and methods currently exist to bypass a blood control septum as part of an infusion procedure, challenges still remain. Accordingly, it would be an improvement in the art to augment or replace current techniques with the system and methods discussed herein.

BRIEF SUMMARY OF THE INVENTION

The present invention has been developed in response to problems and needs in the art that have not yet been fully resolved by currently available systems and methods. Thus, these systems and methods are developed to provide a ported catheter adapter and septum actuator having various features to prevent displacement and dislodging of the septum actuator when accessing the patient's vasculature via the inserted infusion device. Thus, the systems and methods of the present invention provide an intravenous infusion device incorporating a septum actuator with a retention tab that interacts with a retention ring that is incorporated into the valve of a side port. This interaction retains the septum actuator within the lumen of the catheter adapter, thereby allowing for subsequent access to the patient's vasculature.

In some implementations, a ported catheter assembly is provided comprising a catheter adapter having a proximal end, a distal end and a lumen extending therebetween, the catheter adapter further comprising a side port forming a pathway through a sidewall of the catheter adapter and in communication with the lumen. The catheter assembly further comprises a blood control septum disposed within the lumen and dividing the lumen into a proximal chamber and a distal chamber. In some instances, the device further includes a septum actuator having an outer diameter and disposed within the proximal chamber and having a base, a tip and a body extending therebetween. The tip is positioned proximate to the blood control septum and the base is positioned proximate to the proximal end of the catheter adapter. The catheter assembly further comprises an actuator retention tab having an outer diameter and being positioned on an outer surface of the septum actuator body.

The device further comprises a valve disposed within the lumen and forming a seal between the lumen and the pathway of the side port. In some instances, the valve includes a retention ring comprising an inner diameter that is greater than the outer diameter of the septum actuator and less than the outer diameter of the actuator retention tab, wherein the actuator retention tab is positioned on the outer surface of the septum actuator body between the blood control septum and the actuator retention ring.

The valve of the side port generally comprises a flexible tube having an outer diameter that is approximately the same size as an inner diameter of the lumen, whereby the valve is retained within the lumen by an interference fit. The proximal end of the catheter adapter further comprises and opening through which a separate device may be inserted to contact the base of the septum actuator and advance the tip of the septum actuator through a slit of the blood control septum. In some instances, the base comprises an outer diameter that is greater than the inner diameter of the actuator retention ring. As such, the base is prevented from passing through the actuator retention ring. In other instances, the actuator retention ring further comprises a plurality of vents, each vent having a surface area that is selected to prevent or permit passage or air and/or fluid.

In some implementations, the retention tab is spaced from the base of the septum actuator at a distance such that when the base contacts the retention ring the tip of the septum actuator is advanced through the slit of the septum, and the interface between the base and the actuator ring prevents the tip of the septum from further advancement through the slit. In other embodiments, the actuator retention ring is spaced from the base at a first distance, such that when the base contacts the retention ring, the tip of the septum actuator is advance through the septum slit and the interface between the base and the actuator retention ring prevents the tip of the septum actuator from further advancement through the slit. In some instances, the first distance is approximately equal to a second distance between a distal most surface of the tip of the septum actuator and a distal most surface of the blood control septum when the actuator retention tab is in contact with the actuator retention ring.

In some implementations, an antimicrobial coating is applied to one or more surfaces of the infusion therapy device. In one instance, an antimicrobial coating is applied to the septum actuator retention tab, wherein the septum actuator retention tab is positioned within a fluid pathway through the lumen of the catheter adapter. The antimicrobial coating further includes an antimicrobial agent that is compatible for use in an infusion therapy device. Non-limiting examples of suitable antimicrobial agents include chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element. In some instances, the antimicrobial coating comprises an eluting antimicrobial coating matrix whereby the eluting antimicrobial coating provides a zone of inhibition within a fluid within the lumen of the catheter adapter.

Some implementations of the present invention further include an actuator retention tab device comprising an inner surface configured to receive an outer surface of a septum actuator and be fixedly attached thereto; an outer surface positioned opposite the inner surface and in communication with a fluid pathway of a lumen of the catheter adapter, the outer surface having an outer diameter that is greater than an inner diameter of an actuator retention ring of the catheter adapter, whereby the actuator retention tab is prevented from passing through the actuator retention ring. In some instances, the outer surface of the actuator retention tab is further coated with an antimicrobial coating.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

FIG. 4A is a cross-section rear view of a ported catheter adapter showing a cross-section of the retention ring in accordance with a representative embodiment of the present invention.

FIG. 4B is a cross-section rear view of a ported catheter adapter showing a cross-section of a vented retention ring in accordance with a representative embodiment of the present invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
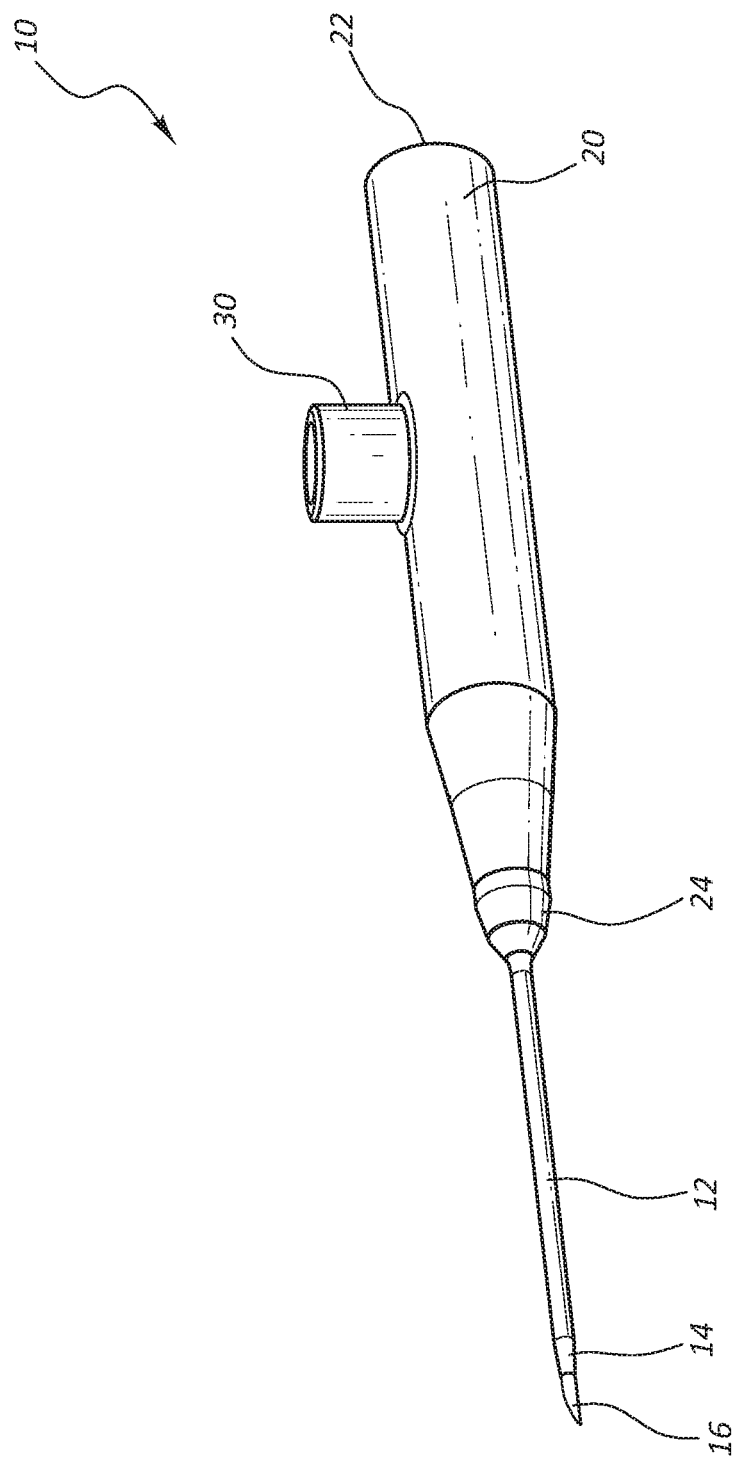
FIG. 1 is a perspective view of a ported infusion therapy device in accordance with a representative embodiment of the present invention.

Referring now to FIG. 1, a ported infusion therapy device 10 is shown. Device 10 generally comprises various features and elements to enable subcutaneous or intravenous infusion of a fluid or medicament into a patient. In some instances, device 10 further comprises feature to enable removal of a fluid from a patient, such as blood.

Device 10 generally comprises a ported catheter adapter 20 having a proximal end 22, a distal end 24 and a lumen 26 extending therebetween. In some instances, catheter adapter 20 further comprises a side port 30 forming a pathway through a sidewall of catheter adapter 20 and in communication with lumen 26. A valve 40 (shown in FIGS. 2-7) is placed within lumen 26 so as to provide a defeatable barrier between side port 30 and lumen 26. Valve 40 generally comprises a resilient, flexible material that is easily deformed when fluid is introduced to port 30 via a syringe or other compatible device. For example, in some instances valve 40 comprises silicone, polyisoprene, or a similar polymer material. Upon deformation of valve 40, fluid from the syringe is permitted to bypass the deformed valve and flow into lumen 26. As the fluid pressure decreases, the resilient nature of the valve's material causes valve 40 to restore its original shape, thereby once again blocking the fluid pathway.

Device 10 further comprises a catheter 12 that is coupled to distal end 24 and which is configured for insertion into a patient. In some instances, catheter 12 comprises a rigid plastic or metallic material having a sharpened distal end that can pierce the patient's skin and gain access to the vasculature or subcutaneous tissues of the patient. In other instance, catheter 12 comprises a flexible material having an inner diameter through which an introducer needle 16 is inserted. Introducer needle 16 comprises a rigid metallic material having a sharpened distal end that extends through catheter 12 and is exposed beyond the tip 14 of catheter 12. The introducer needle is capable of piercing the skin to provide access to the vasculature or subcutaneous tissues of the patient. Once access is obtained, tip 14 of catheter 12 is inserted through the newly formed opening and into the desired location within the patient. Introducer needle 16 is then withdrawn from device 10, and catheter 12 is left disposed within the patient.

Proximal end 22 further comprises an opening 28 for receiving a secondary infusion therapy device 50, such as a syringe or intravenous fluid line. In some instances, proximal end 22 comprises a set of threads configured to threadedly receive the secondary device 50 in a secure manner. Opening 28 may further comprise a tapered opening to receive secondary device 50 via an interference or friction fit. Proximal end 22 and opening 28 may alternatively comprises various surfaces and other features to enable coupling to a needle hub, a diagnostic device, and other suitable infusion therapy equipment.

Figure 2:
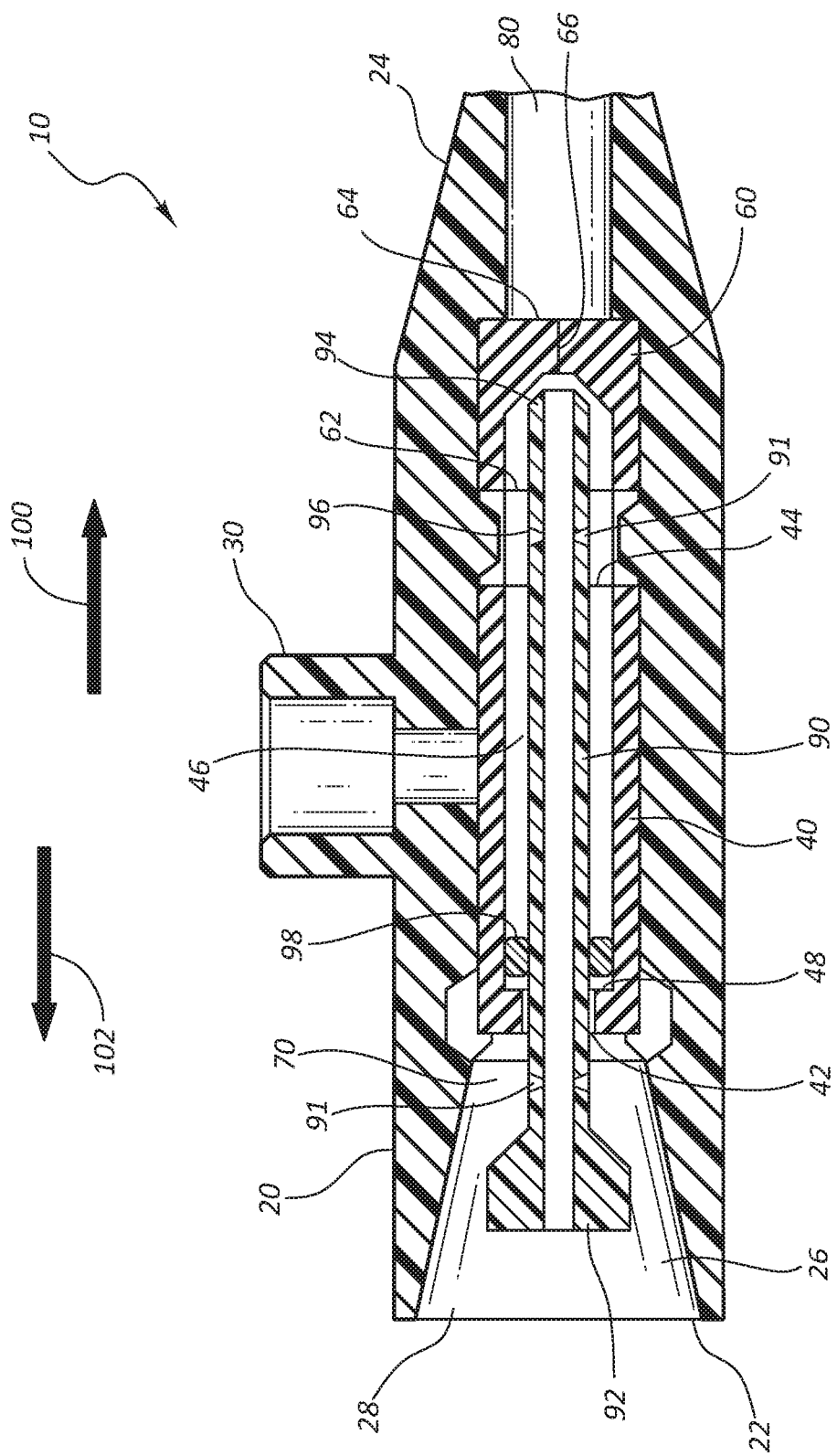
FIG. 2 is a cross-section, side view of a ported catheter adapter having a retention ring, a septum actuator, and an actuator retention tab, and being shown prior to activation in accordance with a representative embodiment of the present invention.

Referring now to FIG. 2, a cross-section side view of a ported catheter adapter 20 is shown. Catheter adapter 20 further comprises a blood control septum 60 that is disposed within lumen 26 towards distal end 24, thereby dividing lumen 26 into proximal 70 and distal 80 fluid chambers. Septum 60 may comprise and shape or structure that is compatible with the teachings of the instant invention. In some instances, septum 60 comprises a cylindrical structure having a proximal opening 62 and a distal membrane 64 comprising a slit 66. Slit 66 provides a fluid-tight seal, thereby preventing fluid from bypassing septum 60.

Septum 60 further comprises a flexible, resilient material that may be selectively deformed to open slit 66 to permit passage of fluids. For example, in some embodiments increased fluid pressure within proximal fluid chamber 70 will result in septum 60 being temporarily deformed, thereby permitting fluid within proximal chamber 70 to bypass septum 60 through slit 66 and flow into distal fluid chamber 80.

In some instances, valve 40 is positioned within lumen 26 at a positioned between opening 28 and blood control septum 60. Valve 40 may be secured within lumen 26 by any compatible means. For example, in some embodiments valve 40 is secured within lumen 26 via an adhesive. In other embodiments, valve 40 is secured within lumen 26 via an interference fit. Further, in some instances valve 40 is inserted into an annular groove formed on the inner surface of lumen 26. Valve 40 is placed within lumen 26 so as to overlap and form a seal between lumen 26 and the pathway of side port 30. Valve 40 comprises a proximal opening 42, a distal opening 44, and a pathway 46 extending therebetween. In some instances, proximal opening 42 comprises a reduced diameter.

In other embodiments, catheter adapter 20 further comprises a septum actuator 90 that is slidably disposed within proximal fluid chamber 70. Septum actuator 90 comprises a base 92, a tip 94, and a body 96 extending therebetween. Septum actuator 90 further comprises a hollow interior through which a fluid may pass. In some instances, septum actuator 90 further comprises one or more fluid vents forming a fluid pathway through a sidewall of septum actuator 90 and in communication with lumen 26, thereby providing diverse flow patterns for a fluid passing through lumen 26 and septum actuator 90.

Figure 3:
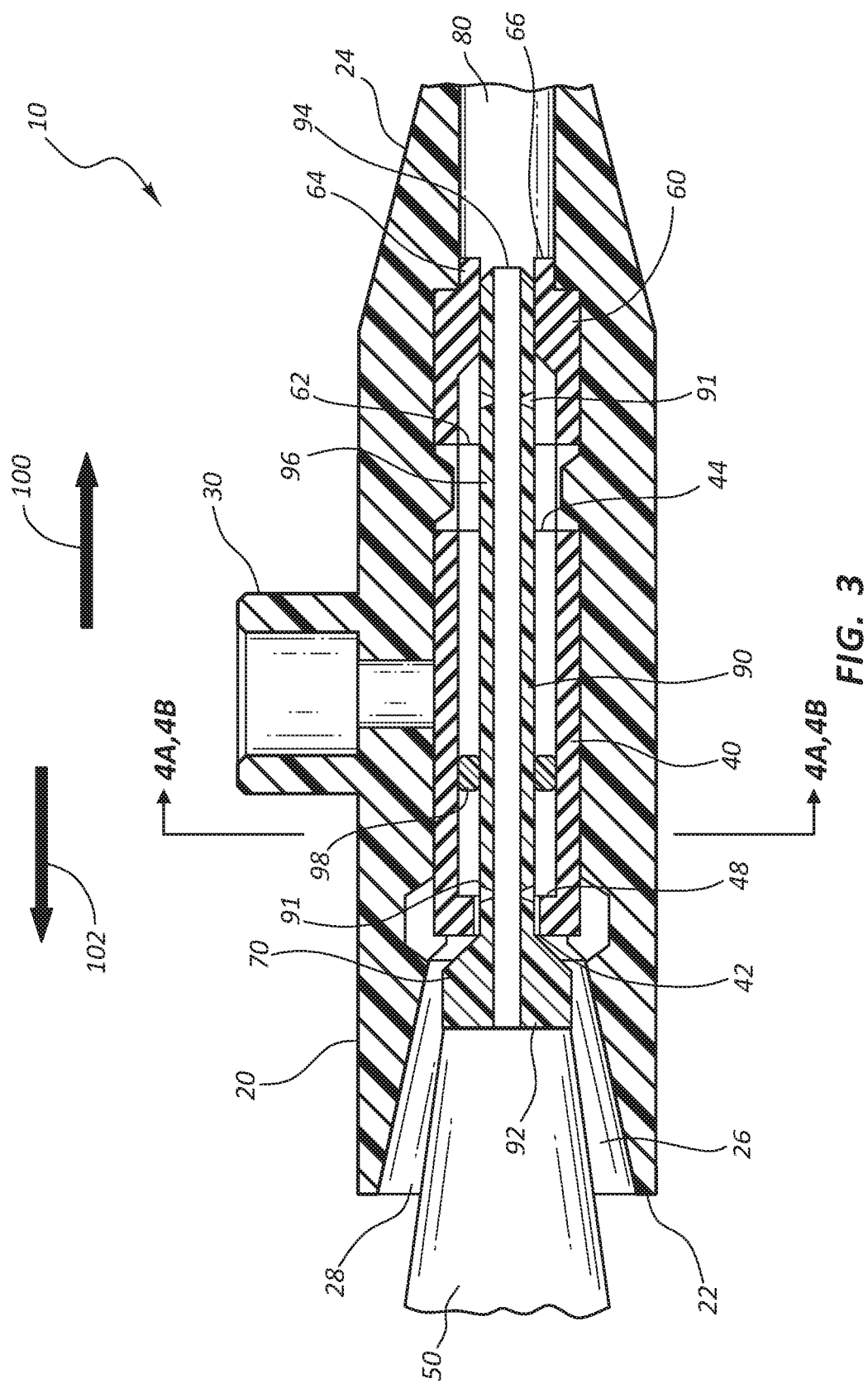
FIG. 3 is a cross-section, side view of a ported catheter adapter having a retention ring, a septum actuator, and an actuator retention tab, and being shown following activation in accordance with a representative embodiment of the present invention.

Base 92 is generally positioned proximate to opening 28 of catheter adapter 20, thereby being accessible to a secondary infusion therapy device 50. Tip 94 is positioned proximate to septum 60, and in some embodiments is inserted within proximal opening 62 and in direct proximity to membrane 64 and slit 66. Tip 94 is advanced through slit 66 as base 92 is pushed in distal direction 100 by a secondary infusion therapy device 50 that is inserted through opening 28, as shown in FIG. 3. Upon removal of secondary device 50, the resilient nature of septum 60 causes membrane 64 to restore its original formation, thereby backing tip 94 out of slit 66, and sliding septum actuator 90 in proximal direction 102, thereby restoring the fluid-tight seal of slit 66.

With continued reference to FIGS. 2 and 3, septum actuator 90 further comprises an actuator retention tab 98. In some instances, retention tab 98 comprises an annular protrusion on the outer surface of body 96. In other embodiments, retention tab 98 comprises an annular ring that is fitted onto the outer surface of body 96. Further still, in some embodiments retention tab 98 comprises one or more protrusions having an effective diameter smaller than pathway 46 and larger than proximal opening 42. Thus, retention tab 98 may comprise various structural configurations.

Retention tab 98 is located on body 96 so as to be positioned within pathway 46 of valve 40. Retention tab 98 comprises an outer diameter that is greater than the outer diameter of body 96 and less than an inner diameter of pathway 46, thereby permitting retention tab 98 to slide freely within pathway 46 of valve 40.

Further, the outer diameter of retention tab 98 is greater than a minimum diameter of proximal opening 42. As such, proximal opening 42 comprises a retention ring 48 that prevents retention tab 98 from bypassing proximal opening 42 in proximal direction 102. Thus, retention tab 98 and retention ring 48 prevent removal of septum actuator 90 through opening 28 of catheter adapter 20.

In some embodiments, retention tab 98 is positioned on septum actuator body 96 at a distance from base 92, such that base 92 contacts a proximal surface of retention ring 48 when tip 94 is advanced through slit 66 to a desired depth. For example, in some instances it may be desirable to prevent over-insertion of tip 94 through slit 66. Over-insertion may be understood to describe a penetration depth of tip 94 into slit 66 where septum 60 is incapable of backing tip 94 out of slit 66 when secondary infusion device 50 is removed from opening 28. Over-insertion of tip 94 into slit 66 may thus prevent slit 66 from reforming a fluid-tight seal. Accordingly, in some embodiments, contact between base 92 and a proximal surface of retention ring 48 prevents additional advancement of tip 94 in distal direction 100, thereby preventing over-insertion.

Similarly, retention tab 98 is positioned on septum actuator body 96 at a distance from base 92, such that tip 94 of septum actuator 90 is permitted to penetrate slit 66 of septum 60 to a minimum insertion depth. Minimum insertion depth may be understood to describe a penetration depth of tip 94 into slit 66 where the surface area of the opening provided in slit 66 is greater than or equal to the surface area of the opening of tip 94. As such, the minimum insertion depth through slit 66 provides an opening or fluid pathway through septum 60 that does not impede or interfere with the flow of fluid passing through septum actuator 90. Thus, the position of retention ring 98 relative to the positions of base 92 and tip 94 ensure proper insertion depth of tip 94 through slit 66 of septum 60.

Referring now to FIGS. 4A and 4B, retention ring 48 of valve 40 generally comprises an inner diameter that is greater than the outer diameter of septum actuator 90. As such, septum actuator 90 may freely slide proximally and distally though retention ring 48. In some instances, retention ring 48 comprises a continuous annular surface that approximates the outer surface of septum actuator 90. A small gap 47 is provided between septum actuator 90 and valve 40, thereby permitting free unhindered movement of septum actuator 90 through retention ring 48, as shown in FIG. 4A. In some instances, gap 47 limits the rate at which fluid and/or air is able to bypass retention ring 48. For example, in some instances gap 47 comprises a surface area sufficient to permit passage of air and fluid at a desire flow rate. In other embodiments, gap 47 comprises a surface area sufficient to permit passage of air, yet prevent passage of a fluid. Further, in at least one embodiment gap 47 comprises a surface area sufficient to prevent passage of air and fluid. Thus, gap 47 may be configured to control oe prevent flashback of blood and other fluid through catheter adapter 20.

In other embodiments, retention ring 48 comprises a plurality of vents 49 arranged in an annular pattern around proximal opening 42. Vents 49 may comprise any surface area as may be desired to affect the flow of fluid and/or air through catheter adapter 20. For example, in some embodiments vents 49 each comprise a surface area sufficient to permit passage of fluid and air at a desired rate. In other embodiments, vents 49 comprise a surface area sufficient to permit passage of air at a desired rate, yet prevent passage of a fluid. Further still, in some embodiments vents 49 comprise a surface area that prevents passage of air and fluid.

In some instances, plurality of vents 49 reduces the stiffness or rigidity of valve 40. As such, valve 40 may more easily be deformed when fluid is injected into side port 30. Thus, in some instances the number and size of vents 49 is selected to achieve a desired stiffness or rigidity for valve 40.

Figure 5:
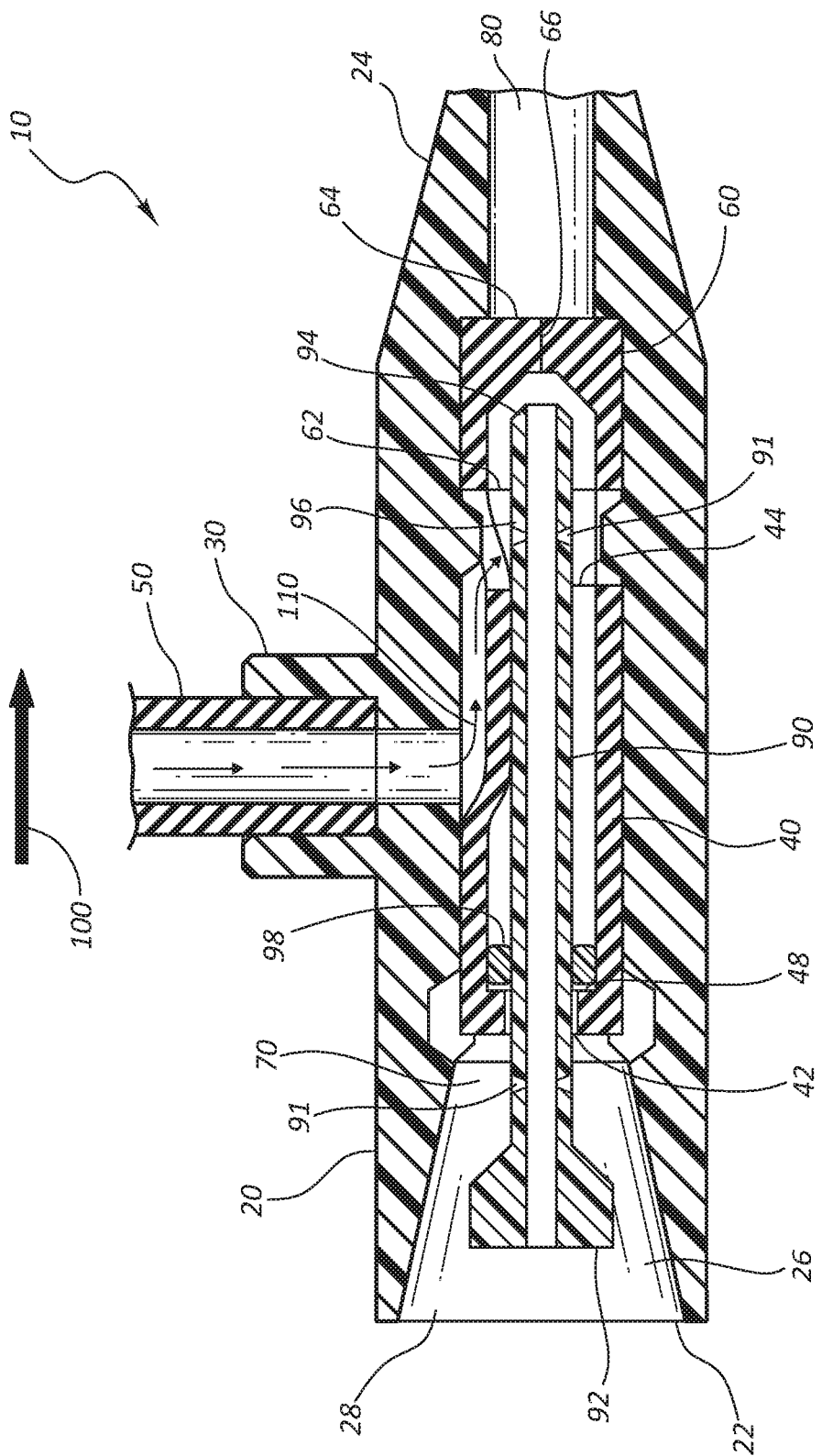
FIG. 5 is a cross-section side view of a ported catheter adapter having a proximally positioned actuator retention ring and undergoing injection of a fluid via the catheter port in accordance with a representative embodiment of the present invention.

Referring now to FIG. 5, a cross-section side view of a ported catheter device 10 undergoing injection of a fluid 110 is shown. Valve 40 generally comprises a flexible polymer tube that may be readily deformed by a fluid 110 that is injected into side port 30 via a secondary infusion device 50. In some instances, retention ring 48 and retention tab 98 are positioned between proximal opening 28 and side port 30. As such, the distal end or opening 48 of valve 40 is deformed and partially collapses as fluid 110 is injected into side port 30. Fluid 110 passes between the outer surface of valve 40 and the inner surface of lumen 26 in distal direction 100 toward blood control septum 60. In some instances, fluid 110 passes between the outer surface of valve 40 and the inner surface of lumen 26 in a proximal direction towards retention ring 48.

In some instances, pressure buildup in proximal fluid chamber due to fluid 110 causes slit 66 of septum 60 to partially open, thereby permitting fluid 110 to bypass septum 60 and flow into distal fluid chamber 80. In other instances, fluid 110 remains within proximal fluid chamber 70 until septum actuator 90 is advanced through slit 66to provide a pathway through septum 60.

Figure 6:
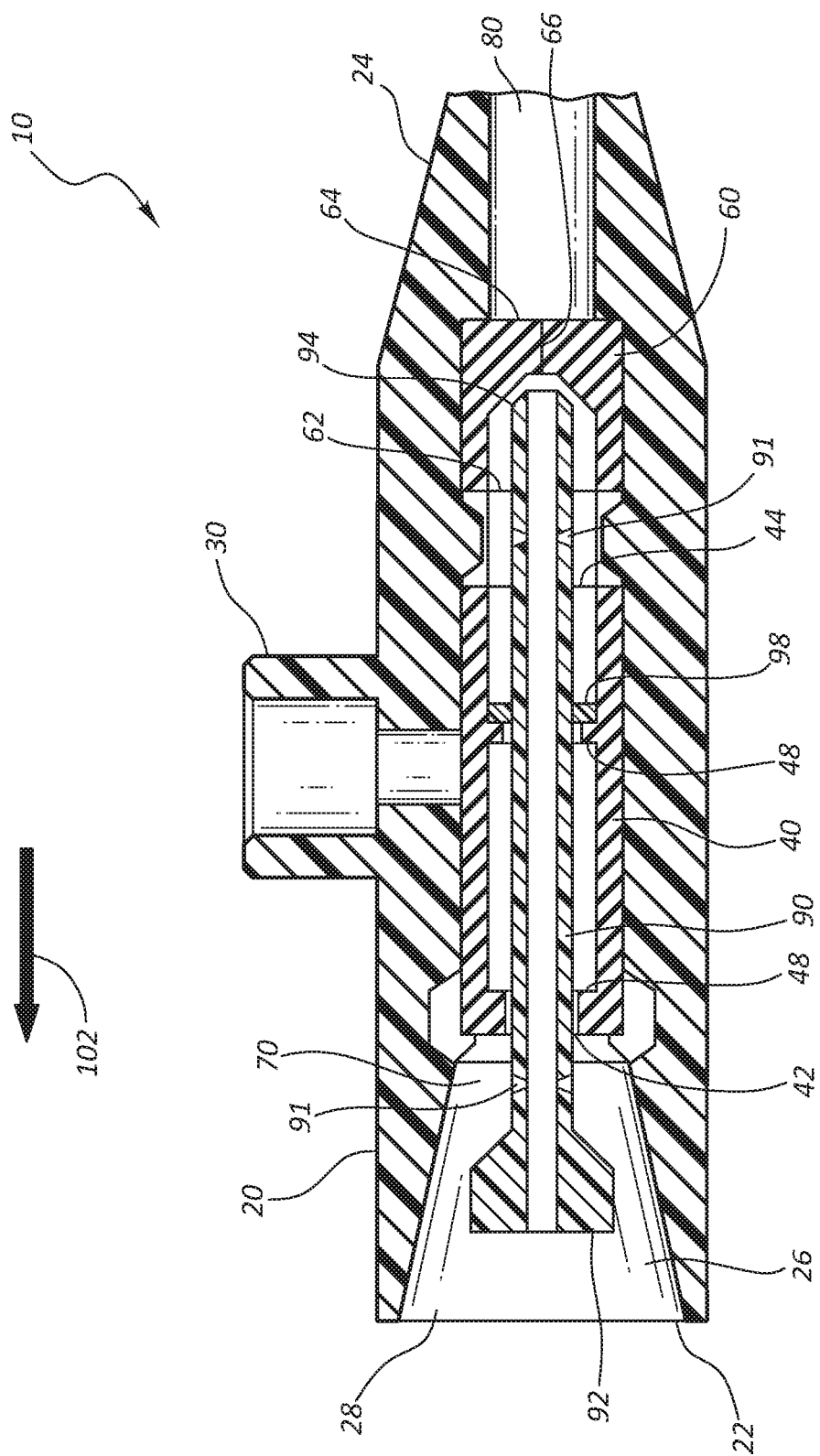
FIG. 6 is a cross-section side view of a ported catheter having a distally positioned actuator retention ring in accordance with a representative embodiment of the present invention.

In other embodiments, retention ring 48 is positioned proximate to the middle of valve 40 and at a position that is between side port 30 and blood control valve 60, as shown in FIG. 6. Retention tab 98 is positioned distally to retention ring 48 and at a position that is between retention ring 48 and blood control valve 60. Proximal opening 42 remains positioned on the proximal end of valve 40 and at a position that is between side port 30 and proximal opening 28. Thus, the distance between base 92 and proximal opening 42 prevents over-insertion, while ensuring a minimum insertion depth of tip 94 through slit 66, as discussed above.

Figure 7:
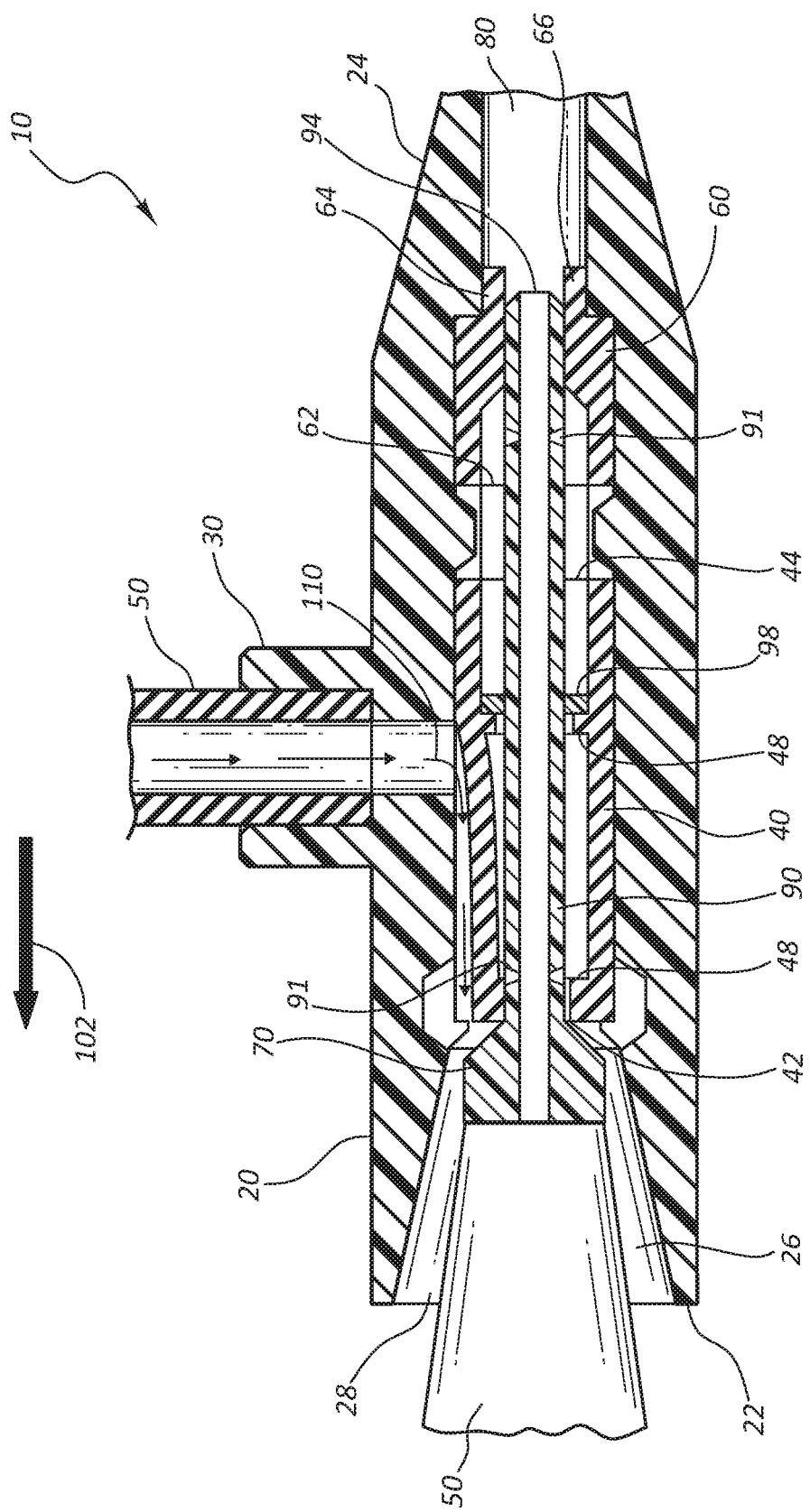
FIG. 7 is a cross-section side view of a ported catheter having a distally positioned actuator retention ring and undergoing injection of a fluid via the catheter port in accordance with a representative embodiment of the present invention.

The distal positions of retention ring 48 and retention tab 98 provide rigidity to the portion of valve 40 located between side port 30 and septum 60. As such, the proximal end or opening 42 of valve 40 is deformed and partially collapses as fluid 110 is injected into side port 30, as shown in FIG. 7. Fluid 110 passes between the outer surface of valve 40 and inner surface of lumen 26 in proximal direction 102 towards proximal opening 28. Upon removal of secondary infusion device 50 from side port 30, the resilient nature of valve 40 restores the fluid tight seal between valve 40 and side port 30, thereby preventing fluid 110 from exiting catheter adapter 20 via side port 30. For this configuration, fluid 110 is generally injected via side port 30 when a secondary infusion device 50 is coupled to proximal opening 28. Thus, fluid 110 may flow through a vent 91 of septum actuator 90, or through proximal opening 42 and into distal fluid chamber 80 via an opening provided through septum 60 by septum actuator 90.

Some embodiments of the present invention further comprise an antimicrobial agent that is applied to one or more surfaces of the infusion therapy device 10 as an antimicrobial coating. The antimicrobial agent may comprise any material or combination of materials that are compatible for use on an intravenous device. Non-limiting examples of suitable antimicrobial agents include chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

The antimicrobial agent is applied to one or more surfaces of the infusion therapy device 10 in a coating matrix that permits the antimicrobial agent to be eluted from the matrix when exposed to a fluid within the catheter adapter. Thus, the eluted antimicrobial agent provides a zone of inhibition around the coating surface or component of the infusion therapy device 10. For example, in some instances the retaining tab 98 is coated with an antimicrobial coating matrix comprising an antimicrobial agent that is capable of eluting out of the coating matrix when the coating matrix is exposed to a fluid. Thus, the antimicrobial agent provides a zone of inhibition around the retention tab. Further, the antimicrobial agent provides antimicrobial properties to the fluid that bypasses the retention tab as it moves through the catheter adapter. Thus, the antimicrobial coating matrix may provide a zone of inhibition to the fluid and other surfaces of the infusion therapy device 10 that are downstream from the coated component.

One having skill in the art will appreciate that the coating matrix and eluting antimicrobial agent may be applied to one or more surfaces of the infusion therapy device 10. For example, in some embodiments one or more of the following components or surfaces of the infusion therapy device 10 is coated with a coating matrix comprising an eluting antimicrobial agent: lumen 26, retention tab 98, septum actuator 90, blood control septum 60, proximal fluid chamber 70, distal fluid chamber 80, valve 40, and side port 30. In other embodiments, a surface or component of infusion therapy device 10 that is positioned in a fluid pathway of the device is coated with an antimicrobial coating and agent, as described herein.

Some embodiments of the present invention further comprise one or more methods for manufacturing a ported catheter assembly according to the teachings of the instant invention. For example, in at least one embodiment a method of manufacturing is provided comprising the following steps: 1) providing a catheter adapter having a proximal end, a distal end and a lumen extending therebetween; 2) placing a side port on a sidewall of the catheter adapter and forming a pathway through the sidewall of the catheter adapter and in communication with the lumen: 3) disposing a blood control septum within the lumen and dividing the lumen into a proximal chamber and a distal chamber; 4) disposing a septum actuator within the proximal chamber of the lumen, the septum actuator having a base, a tip and a body extending therebetween, the tip being positioned proximate to the blood control septum and the base being positioned proximate to the proximal end of the catheter adapter, the septum actuator further comprising an outer diameter; 5) positioning an actuator retention tab on an outer surface of the body, the actuator retention tab having an outer diameter; and 6) disposing a valve within the lumen and forming a seal between the lumen and the pathway of the side port, the valve having a retention ring comprising an inner diameter that is greater than the outer diameter of the septum actuator and less than the outer diameter of the actuator retention tab, wherein the actuator retention tab is positioned on the outer surface of the body between the blood control septum and the actuator retention ring. The method may further comprise a step for applying an antimicrobial coating to at least one of the lumen 26 of the catheter adapter 20, the valve 40, the septum actuator 90 and the retention clip 98 wherein the antimicrobial coating comprises an eluting antimicrobial coating whereby the eluting antimicrobial coating provides a zone of inhibition within a fluid within the lumen of the catheter adapter. In some instances, a further step is provided for providing a plurality of vents within the actuator retention ring.

The ported catheter may alternatively be assembled by first inserting the valve into the lumen, and then inserting the actuator, wherein the retention tabs of the actuator snap past the retention ring of the valve. The valve material is resilient and therefore easily deforms to allow the actuator retention tabs to pass, thereafter resuming its original conformation.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A ported catheter assembly, comprising:
    a catheter adapter having a proximal end, a distal end and a lumen extending therebetween, the catheter adapter further comprising a side port forming a pathway through a sidewall of the catheter adapter and in communication with the lumen;
    a blood control septum disposed within the lumen and dividing the lumen into a proximal chamber and a distal chamber;
    a septum actuator having an outer diameter and disposed within the proximal chamber and having a base, a tip and a body extending therebetween;
    an actuator retention tab having an outer diameter and positioned on an outer surface of the body; and
    a valve disposed within the lumen and forming a seal between the lumen and the pathway of the side port, the valve having a retention ring comprising an inner diameter that is greater than the outer diameter of the septum actuator and less than the outer diameter of the actuator retention tab, wherein the retention ring is positioned between the side port and the blood control septum, wherein the actuator retention tab is positioned on the outer surface of the body distally to the retention ring and at a position between the retention ring and the blood control septum such that rigidity is provided to a portion of the valve between the side port and the blood control septum and a proximal end of the valve collapses in response to fluid being injected into the side port, wherein the valve comprises a flexible tube having an outer diameter that is approximately the same size as an inner diameter of the lumen, whereby the valve is retained within the lumen by an interference fit.

2. The assembly of claim 1, wherein the proximal end of the catheter adapter further comprises an opening through which a separate device may be inserted to contact the base of the septum actuator and advance the tip of the septum actuator through a slit of the blood control septum.

3. The assembly of claim 1, wherein the retention ring is a first retention ring, wherein the valve further comprises a second retention ring, wherein the base comprises an outer diameter that is greater than an inner diameter of the second retention ring.

4. The assembly of claim 3, wherein the second retention ring further comprises a plurality of vents.

5. The assembly of claim 3, wherein when the base contacts the second retention ring, the tip of the septum actuator is advanced through a slit of the septum and an interface between the base and the second retention ring prevents the tip of the septum actuator from further advancement through the slit.

6. The assembly of claim 3, wherein the second retention ring is disposed at a proximal end of the valve.

7. The assembly of claim 1, further comprising an antimicrobial coating applied to the actuator retention tab, wherein the actuator retention tab is positioned within a fluid pathway through the lumen of the catheter adapter.

8. The assembly of claim 7, wherein the antimicrobial coating comprises an antimicrobial agent selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

9. The assembly of claim 7, wherein the antimicrobial coating comprises an eluting antimicrobial coating whereby the eluting antimicrobial coating provides a zone of inhibition within a fluid within the lumen of the catheter adapter.

10. The assembly of claim 1, wherein the tip is positioned proximate to the blood control septum and the base is positioned proximate to the proximal end of the catheter adapter.

11. A ported catheter assembly, comprising:
a catheter adapter having a proximal end, a distal end, and a lumen extending therebetween, the catheter adapter further comprising a side port forming a pathway through a sidewall of the catheter adapter and in communication with the lumen;
a blood control septum disposed within the lumen and dividing the lumen into a proximal chamber and a distal chamber;
a septum actuator having an outer diameter and disposed within the proximal chamber and having a base, a tip and a body extending therebetween, the actuator having a vent forming a fluid pathway through a sidewall of the septum actuator;
an actuator retention tab having an outer diameter and positioned on an outer surface of the body; and
a valve disposed within the lumen and forming a seal between the lumen and the pathway of the side port, the valve having a first retention ring comprising an inner diameter that is greater than the outer diameter of the septum actuator and less than the outer diameter of the actuator retention tab, the valve having a second retention ring being disposed at a proximal end of the valve.

12. The assembly of claim 11, wherein the base comprises an outer diameter that is greater than an inner diameter of the second retention ring.

13. The assembly of claim 12, wherein when the base contacts the second retention ring, the tip of the septum actuator is advanced through a slit of the septum and an interface between the base and the second retention ring prevents the tip of the septum actuator from further advancement through the slit.

14. The assembly of claim 11, wherein the valve comprises a flexible tube having an outer diameter that is approximately the same size as an inner diameter of the lumen, whereby the valve is retained within the lumen by an interference fit.

15. The assembly of claim 11, wherein the proximal end of the catheter adapter further comprises an opening through which a separate device may be inserted to contact the base of the septum actuator and advance the tip of the septum actuator through a slit of the blood control septum.

16. The assembly of claim 11, wherein the second retention ring further comprises a plurality of vents.

17. The assembly of claim 11, further comprising an antimicrobial coating applied to the actuator retention tab, wherein the actuator retention tab is positioned within a fluid pathway through the lumen of the catheter adapter.

18. The assembly of claim 17, wherein the antimicrobial coating comprises an antimicrobial agent selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

19. The assembly of claim 17, wherein the antimicrobial coating comprises an eluting antimicrobial coating whereby the eluting antimicrobial coating provides a zone of inhibition within a fluid within the lumen of the catheter adapter.

20. A ported catheter assembly, comprising:
a catheter adapter having a proximal end, a distal end and a lumen extending therebetween, the catheter adapter further comprising a side port forming a pathway through a sidewall of the catheter adapter and in communication with the lumen;
a blood control septum disposed within the lumen and dividing the lumen into a proximal chamber and a distal chamber;
a septum actuator having an outer diameter and disposed within the proximal chamber and having a base, a tip and a body extending therebetween, wherein the proximal end of the catheter adapter further comprises an opening through which a separate device may be inserted to contact the base of the septum actuator and advance the tip of the septum actuator through a slit of the blood control septum;
an actuator retention tab having an outer diameter and positioned on an outer surface of the body; and
a valve disposed within the lumen and forming a seal between the lumen and the pathway of the side port, the valve having a retention ring comprising an inner diameter that is greater than the outer diameter of the septum actuator and less than the outer diameter of the actuator retention tab, wherein the retention ring is positioned between the side port and the blood control septum, wherein the actuator retention tab is positioned on the outer surface of the body distally to the retention ring and at a position between the retention ring and the blood control septum such that rigidity is provided to a portion of the valve between the side port and the blood control septum and a proximal end of the valve collapses in response to fluid being injected into the side port.

21. A ported catheter assembly, comprising:
a catheter adapter having a proximal end, a distal end and a lumen extending therebetween, the catheter adapter further comprising a side port forming a pathway through a sidewall of the catheter adapter and in communication with the lumen;
a blood control septum disposed within the lumen and dividing the lumen into a proximal chamber and a distal chamber;
a septum actuator having an outer diameter and disposed within the proximal chamber and having a base, a tip and a body extending therebetween;
an actuator retention tab having an outer diameter and positioned on an outer surface of the body;

an antimicrobial coating applied to the actuator retention tab, wherein the actuator retention tab is positioned within a fluid pathway through the lumen of the catheter adapter; and a valve disposed within the lumen and forming a seal between the lumen and the pathway of the side port, the valve having a retention ring comprising an inner diameter that is greater than the outer diameter of the septum actuator and less than the outer diameter of the actuator retention tab, wherein the retention ring is positioned between the side port and the blood control septum, wherein the actuator retention tab is positioned on the outer surface of the body distally to the retention ring and at a position between the retention ring and the blood control septum such that rigidity is provided to a portion of the valve between the side port and the blood control septum and a proximal end of the valve collapses in response to fluid being injected into the side port.

22. The assembly of claim 21, wherein the antimicrobial coating comprises an antimicrobial agent selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

23. The assembly of claim 21, wherein the antimicrobial coating comprises an eluting antimicrobial coating whereby the eluting antimicrobial coating provides a zone of inhibition within a fluid within the lumen of the catheter adapter.

24. A ported catheter assembly, comprising:

a catheter adapter having a proximal end, a distal end and a lumen extending therebetween, the catheter adapter further comprising a side port forming a pathway through a sidewall of the catheter adapter and in communication with the lumen;

a blood control septum disposed within the lumen and dividing the lumen into a proximal chamber and a distal chamber;

a septum actuator having an outer diameter and disposed within the proximal chamber and having a base, a tip and a body extending therebetween, wherein the tip is positioned proximate to the blood control septum and the base is positioned proximate to the proximal end of the catheter adapter;

an actuator retention tab having an outer diameter and positioned on an outer surface of the body; and a valve disposed within the lumen and forming a seal between the lumen and the pathway of the side port, the valve having a retention ring comprising an inner diameter that is greater than the outer diameter of the septum actuator and less than the outer diameter of the actuator retention tab, wherein the retention ring is positioned between the side port and the blood control septum, wherein the actuator retention tab is positioned on the outer surface of the body distally to the retention ring and at a position between the retention ring and the blood control septum such that rigidity is provided to a portion of the valve between the side port and the blood control septum and a proximal end of the valve collapses in response to fluid being injected into the side port.

\* \* \* \* \*